United States Patent
Wakamatsu et al.

(10) Patent No.: US 9,084,904 B2
(45) Date of Patent: Jul. 21, 2015

(54) COMPOSITION FOR EXTERNAL APPLICATION

(75) Inventors: Kosaburo Wakamatsu, Osaka (JP); Shigeo Shinohara, Osaka (JP); Masahiko Tanaka, Osaka (JP); Fumiki Harano, Osaka (JP); Akihiro Aoki, Osaka (JP); Osamu Takasu, Osaka (JP)

(73) Assignee: OTSUKA PHARMACEUTICAL CO., LTD., Chiyoda-Ku, Tokyo (JP)

( * ) Notice: Subject to any disclaimer, the term of this patent is extended or adjusted under 35 U.S.C. 154(b) by 81 days.

(21) Appl. No.: 12/812,402

(22) PCT Filed: Jan. 8, 2009

(86) PCT No.: PCT/JP2009/050161
§ 371 (c)(1),
(2), (4) Date: Jul. 9, 2010

(87) PCT Pub. No.: WO2009/088050
PCT Pub. Date: Jul. 16, 2009

(65) Prior Publication Data
US 2010/0279972 A1 Nov. 4, 2010

(30) Foreign Application Priority Data
Jan. 11, 2008 (JP) .................................. 2008-004454

(51) Int. Cl.
| | |
|---|---|
| *A01N 43/04* | (2006.01) |
| *A61K 31/70* | (2006.01) |
| *A61K 31/715* | (2006.01) |
| *A61Q 19/08* | (2006.01) |
| *A61K 8/60* | (2006.01) |
| *A61Q 19/00* | (2006.01) |
| *A61Q 19/02* | (2006.01) |
| *A61Q 1/08* | (2006.01) |
| *A61Q 1/10* | (2006.01) |
| *A61Q 19/10* | (2006.01) |

(52) U.S. Cl.
CPC . *A61Q 19/08* (2013.01); *A61K 8/60* (2013.01); *A61K 8/606* (2013.01); *A61Q 19/00* (2013.01); *A61Q 19/02* (2013.01); *A61Q 1/08* (2013.01); *A61Q 1/10* (2013.01); *A61Q 19/10* (2013.01)

(58) Field of Classification Search
None
See application file for complete search history.

(56) References Cited

U.S. PATENT DOCUMENTS

| 4,554,251 | A | * | 11/1985 | Hink, Jr. ....................... 435/348 |
| 6,946,436 | B2 | | 9/2005 | Wakamatsu et al. |
| 7,820,636 | B2 | * | 10/2010 | Okuda et al. .................... 514/45 |
| 2004/0029761 | A1 | | 2/2004 | Wakamatsu et al. |
| 2005/0250710 | A1 | * | 11/2005 | Wakamatsu et al. ............. 514/27 |
| 2007/0280979 | A1 | | 12/2007 | Shinohara et al. |

FOREIGN PATENT DOCUMENTS

| CA | 2 706 185 | 7/2009 |
| EP | 0 180 559 A2 | 5/1986 |
| EP | 1 378 224 | 1/2004 |
| JP | 06-122622 | 5/1994 |
| JP | 2000-119155 | 4/2000 |
| JP | 2001-031549 | 2/2001 |
| JP | 2002-145759 | 5/2002 |
| JP | 2002-234830 | 8/2002 |
| JP | 2002-370986 | 12/2002 |
| JP | 2004-238386 | 8/2004 |
| JP | 2004-323401 | 11/2004 |
| JP | 2006-182746 | 7/2006 |

OTHER PUBLICATIONS

Hirano et al., machine translation of JP2004-323401, retrieved from the internet <http://dossier1.ipdl.inpit.go.jp/AIPN/odse_top_fwi.ipdl?N0000=7401> on Dec. 9, 2011, pp. 1-12.*
English-language International Search Report from the Japanese Patent Office for International Application No. PCT/JP2009/050161, mailing date Feb. 24, 2009.
GNPD—Nouvelle Jeuness Skin Cream, Aug. 1, 2002.
GNPD—Smoothing and Volumising Lip Care, Aug. 1, 2007.
GNPD—Firming Vital Bust Care, Mar. 1, 2007.
Intelligent Cell Renewal Cream, Nov. 2005.
Office Action dated Mar. 3, 2015 for CA Patent Application No. 2711744.
Supplementary European Search Report dated Mar. 23, 2015 for EP Patent Application No. 09700700.9.

* cited by examiner

*Primary Examiner* — Layla Bland
(74) *Attorney, Agent, or Firm* — Finnegan, Henderson, Farabow, Garrett & Dunner, L.L.P.

(57) ABSTRACT

A composition for external use capable of more efficiently deriving the effect of purine substances (and/or salts thereof) including (A) sugar; and (B) at least one member selected from the group consisting of purine substances and salts thereof.

13 Claims, 1 Drawing Sheet

COMPOSITION FOR EXTERNAL APPLICATION

This application is the U.S. National Stage of PCT/JP2009/050161 filed Jan. 8, 2009.

TECHNICAL FIELD

The present invention relates to a composition for external use, containing sugar and a purine substance and/or a salt thereof.

BACKGROUND ART

Various types of skin aging are caused by diverse factors, such as an increase in age, sunlight (ultraviolet radiation) exposure, eating habits, stress, etc. Examples of skin aging include pigmentation that produces blemishes, freckles, chloasmata, etc.; skin dullness; dryness; and wrinkles. Prevention of such skin aging is a great health and aesthetic concern, particularly for women.

Cosmetics containing purine substances were developed as a solution for skin aging. Purine substances are known for their wide-ranging effects, including the suppression of skin pigmentation and the retardation of skin aging. Examples of purine substances include adenine, adenosine, and adenosine phosphate. Examples of compositions for external use containing such purine substances include an O/W emulsion composition containing adenine, etc., (refer to Patent Document 1) and a solid composition formed of an oil-in-water emulsion (refer to Patent Document 2).

Purine substances are phosphorylated in a cell and converted into ATP, which serves as an energy source. When applied to a problem skin area, a composition containing purine substances is percutaneously absorbed, and promotes ATP generation in the cell. The increase in the intracellular ATP level activates the metabolism of skin cells, promotes the cell cycle, and thereby facilitates skin turnover. The facilitation of skin turnover encourages the discharge of old horny cell layers and the provision of new horny cell layers. This stabilizes the water retentivity of the skin and makes the skin softer and more resilient, thereby making the skin smoother and reducing dullness.

However, with the recent trend toward more diverse and advanced physiological effects in external use compositions, there has been a demand for the development of an external use composition that more efficiently utilizes the advantageous effects of the purine substances.

Patent Document 1: Japanese Unexamined Patent 2002-234830
Patent Document 2: Japanese Unexamined Patent 2006-182746

DISCLOSURE OF THE INVENTION

Technical Problem

In view of the aforementioned circumstances, an object of the present invention is to provide a composition for external use that more efficiently exerts the advantageous effects of the purine substances (and/or salts thereof).

Technical Solution

The inventors of the present invention conducted extensive studies to solve the foregoing problem, and found that the combined use of sugar and a purine substance and/or a salt thereof will provide a superior intracellular ATP generation-promotion effect. In particular, the research of the inventors confirmed that the ATP generation-promotion effect becomes significantly effective when the proportion of the sugar is 0.001 to 0.3 parts by weight per part by weight of the purine substance and or a salt thereof. Based on this finding, the inventors of the present invention conducted further research and finally completed the present invention.

The present invention provides the following compositions for external use.

Item 1. A composition for external use, comprising the following Component (A) and Component (B),
(A) sugar;
(B) at least one member selected from the group consisting of purine substances and salts thereof.

Item 2. The composition for external use according to Item 1, wherein Component (A) is glucose.

Item 3. The composition for external use according to Item 1 or 2, wherein Component (B) is an adenosine phosphate.

Item 4. The composition for external use according to any one of Items 1 to 3, wherein Component (B) is adenosine 5'-monophosphate or a salt thereof.

Item 5. The composition for external use according to any one of Items 1 to 4, wherein the proportion of Component (B) is 0.01 to 10 wt %.

Item 6. The composition for external use according to any one of Items 1 to 5, wherein the proportion of Component (A) is 0.00001 to 10 parts by weight per part by weight of Component (B).

Item 7. The composition for external use according to any one of Items 1 to 6, wherein the composition is a cosmetic.

Item 8. The composition for external use according to any one of Items 1 to 6, wherein the composition is used to promote ATP production in the skin.

Item 9. The composition for external use according to any one of Items 1 to 6, wherein the composition is used for whitening, moisturizing, or anti-aging.

Item 10. The composition for external use according to any one of Items 1 to 6, wherein the composition is a basic skin care product.

Item 11. The composition for external use according to Item 10, wherein the basic skin care product is an emulsion, cream, or a lotion.

Item 12. The composition for external use according to any one of Items 1 to 6, wherein the composition is an emulsion, and the proportion of Component (A) is 0.0001 to 5 parts by weight per part by weight of Component (B).

Item 13. The composition for external use according to any one of Items 1 to 6, wherein the composition is a cream, and the proportion of Component (A) is 0.001 to 10 parts by weight per part by weight of Component (B).

Item 14. The composition for external use according to any one of Items 1 to 6, wherein the composition is a lotion, and the proportion of Component (A) is 0.0001 to 5 parts by weight per part by weight of Component (B).

Item 15. The composition for external use according to any one of Items 1 to 6, wherein the composition is used to promote the cell cycle or turnover.

Item 16. A process for promoting ATP production in the skin, comprising applying to skin the following Component (A) and Component (B),
(A) sugar;
(B) at least one member selected from the group consisting of purine substances and salts thereof.

Item 17. A whitening process comprising applying the following substances to skin, (A) sugar; and (B) at least one member selected from the group consisting of purine substances and salts thereof.

Item 18. A moisturizing process comprising applying the following substances to skin, (A) sugar; and (B) at least one member selected from the group consisting of purine substances and salts thereof.

Item 19. A skin anti-aging process comprising applying the following substances to skin, (A) sugar; and (B) at least one member selected from the group consisting of purine substances and salts thereof.

Item 20. Use of the following Component (A) and Component (B) for producing a whitening composition for external use, (A) sugar;

(B) at least one member selected from the group consisting of purine substances and salts thereof.

Item 21. Use of the following Component (A) and Component (B) for producing a moisturizing composition for external use, (A) sugar;

(B) at least one member selected from the group consisting of purine substances and salts thereof.

Item 22. Use of the following Component (A) and Component (B) for producing a skin anti-aging composition for external use, (A) sugar;

(B) at least one member selected from the group consisting of purine substances and salts thereof.

Item 23. Use of a composition for external use containing the following Component (A) and Component (B) for producing a whitening agent, (A) sugar;

(B) at least one member selected from the group consisting of purine substances and salts thereof.

Item 24. Use of a composition for external use containing the following Component (A) and Component (B) for producing a moisturizing agent, (A) sugar;

(B) at least one member selected from the group consisting of purine substances and salts thereof.

Item 25. Use of a composition for external use containing the following Component (A) and Component (B) for producing a skin anti-aging agent, (A) sugar;

(B) at least one member selected from the group consisting of purine substances and salts thereof.

Item 26. The process according to any one of Items 16 to 19 comprising applying the composition for external use according to any one of Items 1 to 6.

Effect of the Invention

The composition for external use of the present invention more effectively exhibits the function of the purine substance and/or salts thereof. Particularly, the composition for external use of the present invention facilitates the expression of the function of AMP (adenosine monophosphate), and thereby continuously and effectively ensures the water retentivity of the skin, superior skin softness, the reduction of pigmentation (reduction in the amount of melanin), superior skin brightness (prevention of dullness), the promotion of the cell cycle, the promotion of turnover, etc., based on the intracellular ATP generation-promotion effect given by AMP.

BEST MODE FOR CARRYING OUT THE INVENTION

The composition for external use for the skin of the present invention contains the following Component (A) and Component (B). The following describes the composition details of the present invention.

(A) Sugar

The sugar used as Component (A) of the present invention is not limited as long as it is pharmacologically or cosmetically acceptable and is percutaneously absorbable. Examples of Component (A) include glucose, monosaccharides having at least one unit of glucose as a componential member and 2 to 12 oligosaccharides.

Examples of sugar include monosaccharides such as fructose, arabinose, or galactose; disaccharides such as sucrose, lactose, maltose or trehalose; and oligosaccharides such as fructo-oligosaccharide, xylo-oligosaccharide, or malto-oligosaccharide. Among these, a monosaccharide or disaccharide having at least one unit of glucose as a componential member is particularly preferable, and glucose is further preferable.

The composition for external use of the present invention may be formed of one member of the sugars listed above, or an arbitrary combination of them. When using more than one kind of sugar, the form of the combination is not limited insofar as the effect of the present invention is not impaired.

The proportion of Component (A) based on its total amount in the composition for external use of the present invention is, for example, not less than 0.0001 wt %, preferably 0.0001 to 10 wt %, more preferably 0.0001 to 5 wt %, and further preferably 0.001 to 1 wt %.

(B) Purine Substance and Salt Thereof.

Component (B), which is used in the composition for external use of the present invention, is at least one member selected from the group consisting of purine substances and salts thereof. In the present invention, a "purine substance" denotes one of various derivatives having a purine or a purine nucleus as a skeleton (hereinafter referred to as a purine substance).

The purine substances usable in the present invention are not particularly limited. Examples of purine substances include adenine, guanine, hypoxanthine, xanthine, adenosine, guanosine, inosine, adenosine phosphates [adenosine 2'-monophosphate, adenosine 3'-monophosphate, adenosine 5'-monophosphate (AMP), cyclic adenosine 3'5'-monophosphate (cAMP), adenosine 5'-diphosphate (ADP), adenosine 5'-triphosphate (ATP)], guanosine phosphates (guanosine 3'-monophosphate, guanosine 5'-monophosphate, guanosine 5'-diphosphate, guanosine 5'-triphosphate), adenylosuccinic acid, xanthylic acid, inosinic acid, flavine adenine dinucleotide (FAD), nicotinamide adenine dinucleotide (NAD) and the like. Preferable among these are adenosine monophosphates (adenosine 2'-monophosphate, adenosine 3'-monophosphate, AMP, and cAMP). AMP is particularly preferred as it makes the effect of the present invention more significant.

The purine substance salts usable in the present invention are also not particularly limited. Examples of such purine substance salts include alkali metal salts such as sodium salts and potassium salts; alkaline earth metal salts such as calcium salts, magnesium salts, and barium salts; salts with basic amino acids such as arginine and lysine; salts of ammoniums such as ammonium, tricyclohexylammonium salts; and salts of alkanolamines such as monoisopropanolamine, diisopropanolamine and triisopropanolamine. Alkali metal salts of purine substances are particularly preferred.

Particularly suitable substances to be used as Component (B) in the present invention are monosodium adenosine monophosphate and disodium adenosine monophosphate.

Component (B) in the composition for external use of the present invention may be formed of one member of the substances above, or an arbitrary combination of them. When using more than one kind, the form of the combination is not limited insofar as the effect of the present invention is not impaired.

The proportion of Component (B) in the composition for external use of the present invention is, for example, not less than 0.01 wt %, preferably 0.1 to 20 wt %, and further preferably 0.1 to 10 wt %, in the gross amount. When Component (B) is a salt of a purine substance, the proportion is converted to the weight of the purine substance.

As long as the composition for external use of the present invention contains both Component (A) and Component (B), the form of the combination of the two components is not restricted. Preferable examples of the combinations of Component (A), sugar, and Component (B), a purine substance and/or a salt thereof, for the external use composition of the present invention include a combination of a monosaccharide as Component (A) and an adenosine phosphate or a salt thereof as Component (B); and a combination of glucose as Component (A) and AMP or a salt thereof as Component (B). These combinations make the superior effect of the present invention even more significant.

The ratio between the purine substance and the sugar in the external use composition of the present invention is not particularly limited, and is set to an appropriate ratio according to the aforementioned proportion ranges of Component (A) and Component (B), the form of the composition, desired effects, etc. For one suitable mixture, the proportion of Component (A) is 0.00001 to 10 parts by weight, preferably 0.0001 to 5 parts by weight, more preferably 0.0001 to 1 parts by weight, and further preferably 0.001 to 0.3 parts by weight per part by weight of Component (B). In particular, when the composition for external use of the present invention contains Component (A) in an amount of 0.001 to 0.3 parts by weight per part by weight of Component (B), the intracellular ATP generation-promotion effect significantly increases. When Component (B) is a salt of a purine substance, the proportion is converted to the weight of the purine substance.

(C) Other Components

The composition for external use of the present invention usually has a pH ranging from that of a weak acid to that of a neutral substance. With a view to minimizing irritation of the skin and alleviating pigmentation, the composition preferably has a pH in the range of 5 to 7 and more preferably 5.5 to 7. pH adjusters may be incorporated into the composition for external use of the present invention so as to control the pH within the above range. Such pH adjusters are not limited insofar as they are weakly alkaline or alkaline and pharmacologically or cosmetically acceptable. Examples of pH adjusters include sodium hydroxide, L-arginine, aminomethylpropanediol, diisopropanolamine, and triethanolamine.

In addition to the above components, the composition for external use of the present invention may contain, as required, a wide variety of components or additives that are generally incorporated into externally applied preparations. Examples of components include surfactants, solubilizers, fats or oils, polyhydric alcohols, viscosity improvers, antiseptics, bactericides, humectants, colorants, dispersants, antioxidants, chelating agents, astringents, whiteners, pigments, deodorizers, and perfumes. Such components may be used singly or in any combination of two or more members.

The composition for external use of the present invention may take any form as long as it is formulated as an externally applied composition for the skin such as a cosmetic, an externally applied medical or quasi-medical drug, etc. More specifically, the composition for external use of the present invention may be produced as externally applicable preparations in desirable forms such as pastes, mousses, gels, liquids, emulsions, suspensions, creams, ointments, sheets, aerosol formulations, spray formulations, liniments, etc., when the above-mentioned components are formulated, as required, into the composition for external use of the invention, and further other solvents or conventionally used bases or carriers for externally applied preparations are added thereinto as required. Such formulations can be prepared using general techniques in this field.

The usage of the composition for external use of the present invention is also not particularly limited. For example, the composition for external use of the present invention can be adopted as various externally applied preparations, such as externally applied medical drugs; externally applied quasi-medical drugs; makeup cosmetics such as foundations, blushers, mascaras, eye shadows, eyeliners, face powders, etc; basic skin care products such as emulsions, creams, lotions, oils and packs; washes such as facial washes, cleansing creams and body washes; cleaning agents; cleaners; bath agents, etc.

In the aforementioned composition for external use, the ratio between Component (A) and Component (B) can be arbitrarily changed depending on the characteristics of the target product. For example, for an emulsion, the amount of Component (A) is 0.0001 to 5 parts by weight, preferably 0.0005 to 1 parts by weight, and more preferably 0.001 to 0.1 parts by weight per part by weight of Component (B); for a cream, the amount of Component (A) is 0.001 to 10 parts by weight, preferably 0.01 to 5 parts by weight, more preferably 0.1 to 1 parts by weight per part by weight of Component (B); for a lotion, the amount of Component (A) is 0.0001 to 5 parts by weight, preferably 0.0005 to 1 parts by weight, and more preferably 0.001 to 0.05 parts by weight per part by weight of Component (B). The resulting composition for external use ensures superior texture, stable viscosity, and stable characters by maintaining the aforementioned proportion ranges.

The composition for external use of the present invention is used by being applied to human skin. The application amount and frequency of the composition for external use of the present invention is not particularly limited. For example, the composition may be applied to the skin (particularly in a problem area with pigmentation (blemishes), wrinkles, dryness, etc.) in a suitable amount once or several times per day, according to the types and/or concentrations of the active ingredients used, the age/gender of the user, the condition of the problem part of the skin, the application method, the effect intended, etc. A generally appropriate amount of the composition for external use of the present invention is 0.5 to 10 mg/cm$^2$.

The composition for external use of the present invention can effectively facilitate the epidermal ATP-generation property through the combined use of Component (A) and Component (B), as shown in the later-described Example. With this function, the composition for external use of the present invention more efficiently ensures the water retentivity of the skin, superior skin softness, the reduction of pigmentation (reduction in the amount of melanin), the diminishment of chloasma, superior skin brightness (prevention of dullness), the promotion of the cell cycle, and the promotion of turnover.

Accordingly, the composition for external use of the present invention is useful as a skin anti-aging composition, a moisturizing composition, a composition for alleviating pigmentation, or as a whitening composition.

In addition to the aforementioned composition for external use, the present invention also provides a whitening method, moisturizing method, or a skin anti-aging method. The method comprises applying Component (A), sugar, and Component (B), at least one member selected from the group consisting of purine substances and salts thereof. As described, by applying Component (A) and Component (B) to the skin, the water retentivity of the skin, superior skin softness, the reduction of pigmentation (reduction in the amount of melanin), the diminishment of chloasma, superior skin brightness (prevention of dullness), the promotion of the cell cycle, and the promotion of turnover can be further improved. The whitening method, moisturizing method, or skin anti-aging method of the present invention applies Component (A) and Component (B) either simultaneously or separately. When separately applying Component (A) and Component (B), the order of application is not limited; either Component (A) or Component (B) can be applied first. The application amounts of the two components are not limited insofar as the excellent effect of the present invention is not impaired. The amounts are determined in reference to the aforementioned suitable proportions of the two components of the composition for external use of the present invention.

The method preferably uses the aforementioned composition for external use of the present invention to further improve the effect of the present invention. The application amount of the composition for external use during the method is also not limited insofar as the excellent effect of the present invention is not impaired, and can be determined also in reference to the aforementioned suitable application amount.

EXAMPLE

The present invention is more specifically explained with reference to the Experiment Examples etc. However, the present invention is not limited to the Examples.

The following reports a test for examining the influence of glucose on the intracellular ATP generation-promotion effect given by AMP. Cultured mouse epidermal cells were used in the test.

Test Method
(1) Materials
  Cells: JB6 CL 41-5A Cell Line, mouse epidermis
  Culture medium: an MEM medium containing 5% FCS (Fetal Calf Serum)
  MEM medium (Nacalai Tesque), Fetal calf serum (GIBCO) AMP: disodium adenosine monophosphate (Yamasa Corporation)
  Glucose: D-glucose (Wako Pure Chemical Ind. Ltd.)
  ATP measurement: "ATPlite" Luminescence Assay System (Perkin Elmer)
(2) Measurement Device
  Microplate luminescence reader Anthos Lucy 1 (Aloka Co., Ltd.)
(3) Procedure
  Cultured mouse epidermal cells were inoculated in a 96-well microplate in an amount of $5.8 \times 10^3$ cells per well. After two hours, the medium was replaced with another culture medium containing a test sample of a predetermined quantity. After another two hours, the medium was removed, and the amount of ATP was measured.

In the following experiment example, the content of glucose was 100 mg/dL, based on the fact that the normal fasting blood-sugar level of a living body is generally about 70 to 100 mg/dL.

Experiment Example 1

Three concentrations (101, 110, 200 mg/dL) of glucose were added to a normal culture medium (containing 100 mg/dL of glucose) so as to examine how each concentration affects the ATP generation-promotion effect of AMP (1 mM). As the glucose content increased from 101 to 110 mg/dL, ATP generation increased. The addition of glucose with a concentration of 110 mg/dL increased ATP generation by 25%, based on the concentration of 100 mg/dL that corresponds to the normal fasting blood-sugar level. In addition, when the glucose content became still higher, at 200 mg/dL, with AMP of 1 mM, ATP generation was lower than when the glucose content was 110 mg/dL and AMP was 1 mM. FIG. 1 shows the result of this experiment.

Experiment Example 2

Based on the result of Experiment Example 1, another experiment was performed as follows so as to confirm the influence of the glucose addition on the ATP generation-promotion effect of AMP by ensuring the increase of ATP generation by AMP (1 mM) when the glucose content is 101 mg/dL and 110 mg/dL, and ensuring the decrease of ATP generation by AMP (1 mM) when the glucose content is 200 mg/dL or higher. General culture medium (containing glucose of 100 mg/dL) was supplied with extra glucose to obtain separate final glucose concentrations of 101, 110, 200, and 600 mg/dL; and the ATP generation was observed for each concentration. FIG. 2 shows the result.

When the glucose content was 101 or 110 mg/dL and AMP was 1 mM, the ATP generation increased by 30% or more, confirming the increase of the ATP generation-promotion effect of AMP. When the glucose content was 200 mg/dL and AMP was 1 mM, the ATP generation was lower than when the glucose content was 100 mg/dL and AMP was 1 mM, confirming the assumed decrease of the ATP generation-promotion effect of AMP. Additionally, though the ATP generation-promotion effect of AMP was small when the glucose content was 600 mg/dL, it was not significantly lower than the amount of ATP generation in an AMP-free medium containing 100 mg/dL glucose (general culture).

The results of Experiment Examples 1 and 2 revealed that the ATP generation-promotion effect of AMP significantly increases when the glucose concentration around the cell falls within a range of 101 to 110 mg/dL. In contrast, under the test conditions, the promotion effect tended to decrease when the glucose concentration around the cell increased to 200 mg/dL.

Considering the fact that the glucose concentration of 100 mg/dL corresponds to the normal fasting blood-sugar level, the Experiment Examples showed that the addition of glucose in an amount of 1 to 10 mg/dL remarkably enhanced the ATP generation-promotion effect of AMP. When AMP was 1 mM and the glucose content was 101 to 110 mg/dL (i.e., 1 to 10 mg/dL of glucose was added), the proportion of the glucose was about 0.028 to 0.289 parts by weight per part by weight of AMP. In more general terms, the experiment showed that the ATP generation-promotion effect of AMP became significant when the proportion of the glucose was approximately 0.02 to 0.3 parts by weight per part by weight of AMP.

The results of the experiment thus showed that the ATP generation-promotion effect of AMP becomes significant when the proportion of the glucose is 0.028 parts by weight per part by weight of AMP. Accordingly, the aforementioned degree of the ATP generation-promotion effect of AMP is likely to be ensured even when the proportion of the glucose is reduced to about 1/30 (0.001 parts by weight), and preferably about 1/10 (0.003 parts by weight) of the amount used in the foregoing experiment, per part by weight of AMP.

Prescription Examples

Some prescription examples of the composition for external use of the present invention are shown below. However, the present invention is not limited to those examples.

| Lotion | |
|---|---|
| Ingredients | Content (wt. %) |
| 1. Cyclic adenosine 3',5'-monophosphate | 0.1 |
| 2. Glucose | 0.03 |
| 3. Dipropylene glycol | 2.0 |
| 4. Concentrated-glycerin | 2.0 |
| 5. Polyoxyethylene sorbitan monolaurate (20E.O.) | 1.0 |
| 6. Polyethylene glycol 1500 | 1.5 |
| 7. Sodium alginate | 0.2 |
| 8. Antiseptic | Suitable amount |
| 9. pH-adjuster | Suitable amount |
| 10. Purified water | Balance |

| Emulsion | |
|---|---|
| Ingredients | Content (wt. %) |
| 1. Disodium adenosine monophosphate | 1.0 |
| 2. Fructose | 0.1 |
| 3. Decaglyceryl monoisostearate | 1.8 |
| 4. Decaglyceryl monomyristate | 0.2 |
| 5. Sodium stearoyl lactate | 0.1 |
| 6. Liquid paraffin | 5.0 |
| 7. Concentrated glycerin | 4.0 |
| 8. Diglycerol | 3.0 |
| 9. Acrylic acid-alkyl methacrylate copolymer | 0.45 |
| 10. Antiseptic | Suitable amount |
| 11. pH-adjuster | Suitable amount |
| 12. Purified water | Balance |

| Cream | |
|---|---|
| Ingredients | Content (wt. %) |
| 1. Disodium adenosine triphosphate | 1.0 |
| 2. Galactose | 0.1 |
| 3. Stearic acid | 3.0 |
| 4. Behenyl alcohol | 2.0 |
| 5. Polyoxyalkylene alkyl covariance silicon | 2.0 |
| 6. Decamethylcyclopentasiloxane | 3.0 |
| 7. Liquid paraffin | 5.0 |
| 8. Glyceryl tri-2-ethylhexanoate | 5.0 |
| 9. Hydrogenated Lecithin | 0.1 |
| 10. Concentrated glycerin | 3.0 |
| 11. Carboxy vinyl polymer | 0.1 |
| 12. dl-α-tocopherol acetate | 0.1 |
| 13. Antiseptic | Suitable amount |
| 14. pH-adjuster | Suitable amount |
| 15. Purified water | Balance |

| Cosmetic lotion | |
|---|---|
| Ingredients | Content (wt. %) |
| 1. Disodium adenosine monophosphate | 2.0 |
| 2. Trehalose | 0.3 |
| 3. 1,3-butylene glycol | 3.0 |
| 4. Concentrated glycerin | 5.0 |
| 5. Sodium hyaluronate | 0.1 |
| 6. Polyoxyethylene methylpolysiloxane copolymer | 0.2 |
| 7. Methoxyethylene maleic anhydride copolymer | 0.2 |
| 8. Ethanol | 3.0 |
| 9. Antiseptic | Suitable amount |
| 10. pH-adjuster | Suitable amount |
| 11. Purified water | Balance |

| Lotion | |
|---|---|
| Ingredients | Content (wt. %) |
| 1. Adenosine monophosphate | 2.0 |
| 2. Glucose | 0.01 |
| 3. 1,3-butylene glycol | 2.0 |
| 4. Concentrated-glycerin | 2.0 |
| 5. Polyethylene glycol 1500 | 1.5 |
| 6. Sodium hyaluronate | 0.01 |
| 7. Ethanol | 5.0 |
| 8. Antiseptic | Suitable amount |
| 9. pH-adjuster | Suitable amount |
| 10. Purified water | Balance |

| Emulsion | |
|---|---|
| Ingredients | Content (wt. %) |
| 1. Disodium adenosine triphosphate | 0.5 |
| 2. Glucose | 0.05 |
| 3. Decaglyceryl diisostearate | 1.2 |
| 4. Decaglyceryl monostearate | 0.8 |
| 5. Stearic acid | 2.0 |
| 6. Glyceryl tri-2-ethylhexanoate | 3.0 |
| 7. α-olefin oligomer | 2.0 |
| 8. Concentrated glycerin | 5.0 |
| 9. 1,3-butylene glycol | 3.0 |
| 10. Carboxy vinyl polymer | 0.1 |
| 11. Antiseptic | Suitable amount |
| 12. pH-adjuster | Suitable amount |
| 13. Purified water | Balance |

| Cream | |
|---|---|
| Ingredients | Content (wt. %) |
| 1. Disodium adenosine monophosphate | 1.0 |
| 2. Glucose | 0.3 |
| 3. Decaglyceryl monomyristate | 1.5 |
| 4. Self-emulsifying glyceryl monostearate | 0.9 |
| 5. Cetyl-alchohol | 2.0 |
| 6. Stearyl-alcohol | 1.0 |
| 7. Cetyl palmitate | 2.0 |
| 8. Liquid paraffin | 8.0 |
| 9. Concentrated glycerin | 6.0 |
| 10. Polyethylene glycol 1000 | 2.0 |
| 11. Hydrogenated Lecithin | 0.1 |
| 12. 1,2-pentanediol | 3.0 |
| 13. Acrylic acid-alkyl methacrylate copolymer | 0.15 |
| 14. Antiseptic | Suitable amount |

-continued

| Cream | |
|---|---|
| Ingredients | Content (wt. %) |
| 15. pH-adjuster | Suitable amount |
| 16. Purified water | Balance |

These formulations in the Prescription Examples all securely exhibited the aforementioned effects of the present invention.

Figure 1:
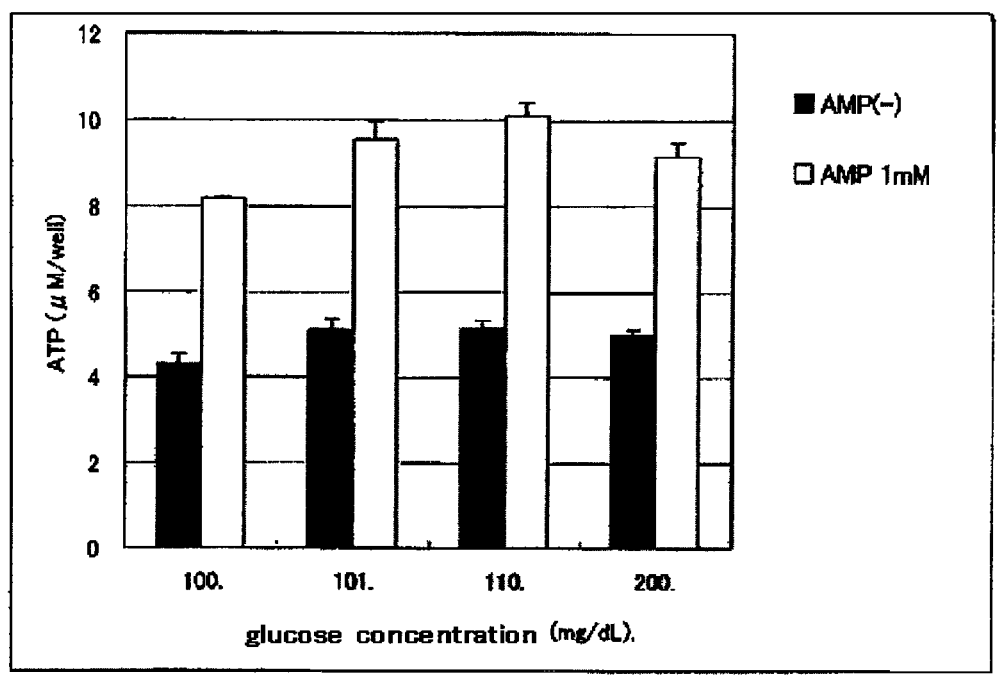
FIG. 1 is a graph showing an influence of glucose on the intracellular ATP generation promotion effect of AMP, according to Experiment Example 1.
Figure 2:
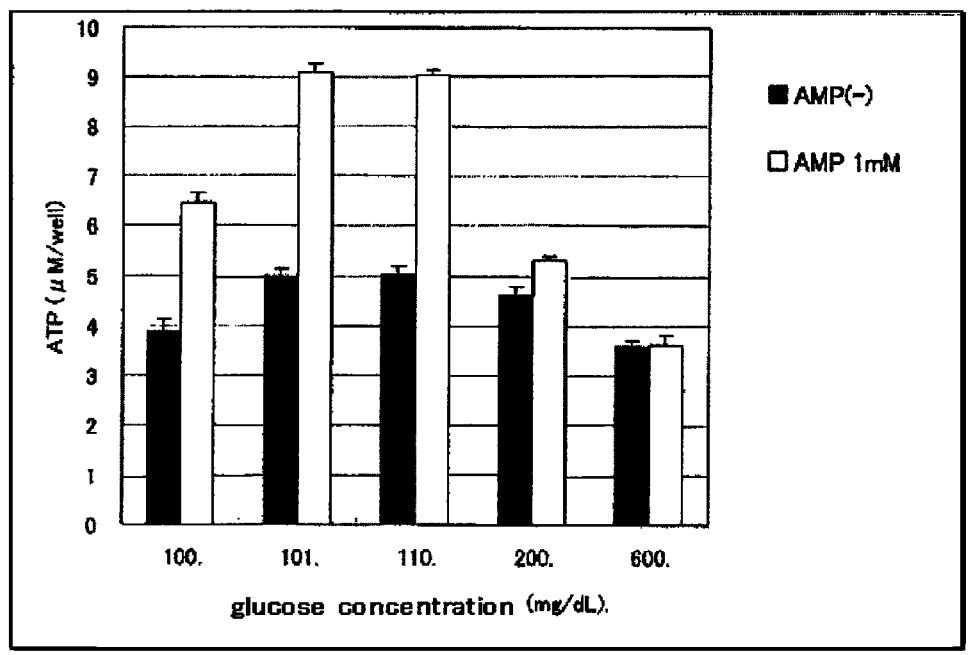
FIG. 2 is a graph showing an influence of glucose on the intracellular ATP generation promotion effect of AMP, according to Experiment Example 2.

The invention claimed is:

1. A composition for external use, comprising the following Component (A) and Component (B),
   (A) at least one member selected from the group consisting of glucose, maltose and trehalose;
   (B) at least one member selected from the group consisting of adenosine monophosphate and salts thereof,
   wherein the proportion of Component (A) is 0.001 to 0.3 parts by weight per part by weight of Component (B), and the proportion of Component (B) is 0.1 to 10 wt %.

2. The composition for external use according to claim 1, wherein Component (A) is glucose.

3. The composition for external use according to claim 1, wherein Component (B) is adenosine 5'-monophosphate or a salt thereof.

4. The composition for external use according to claim 1, wherein the composition is a cosmetic.

5. The composition for external use according to claim 1, wherein the composition is used for whitening, moisturizing, or anti-aging.

6. A whitening process comprising applying the following substances to skin,
   (A) at least one member selected from the group consisting of glucose, maltose and trehalose; and
   (B) at least one member selected from the group consisting of adenosine monophosphate and salts thereof,
   wherein the proportion of Component (A) applied is 0.001 to 0.3 parts by weight per part by weight of Component (B), and the proportion of Component (B) is 0.1 to 10 wt %.

7. A moisturizing process comprising applying the following substances to skin,
   (A) at least one member selected from the group consisting of glucose, maltose and trehalose; and
   (B) at least one member selected from the group consisting of adenosine monophosphate and salts thereof,
   wherein the proportion of Component (A) applied is 0.001 to 0.3 parts by weight per part by weight of Component (B), and the proportion of Component (B) is 0.1 to 10 wt %.

8. A skin anti-aging process comprising applying the following substances to skin,
   (A) at least one member selected from the group consisting of glucose, maltose and trehalose; and
   (B) at least one member selected from the group consisting of adenosine monophosphate and salts thereof,
   wherein the proportion of Component (A) applied is 0.001 to 0.3 parts by weight per part by weight of Component (B), and the proportion of Component (B) is 0.1 to 10 wt %.

9. A composition for external use, producing by the addition of the following Component (A) to a composition which contains an active ingredient consisting essentially of the following Component (B), wherein the proportion of Component (A) is 0.001 to 0.3 parts by weight per part by weight of Component (B) and the proportion of Component (B) is 0.1 to 10 wt % based on the composition for external use;
   (A) at least one member selected from the group consisting of glucose, maltose and trehalose;
   (B) at least one member selected from the group consisting of adenosine monophosphate and salts thereof.

10. A composition for external use, comprising the following Component (A) and Component (B), whose active ingredient consists essentially of Component (B),
    (A) at least one member selected from the group consisting of glucose, maltose and trehalose;
    (B) at least one member selected from the group consisting of adenosine monophosphate and salts thereof;
    wherein the proportion of Component (A) is 0.001 to 0.3 parts by weight per part by weight of Component (B), and the proportion of Component (B) is 0.1 to 10 wt %.

11. A whitening process, moisturizing process or skin anti-aging process comprising applying to skin a composition for external use, comprising the following Component (A) and Component (B),
    (A) at least one member selected from the group consisting of glucose, maltose and trehalose;
    (B) at least one member selected from the group consisting of adenosine monophosphate and salts thereof,
    wherein the proportion of Component (A) is 0.001 to 0.3 parts by weight per part by weight of Component (B), and the proportion of Component (B) is 0.1 to 10 wt %.

12. A composition for external use, comprising the following Component (A) and Component (B),
    (A) at least one member selected from the group of glucose, maltose and trehalose or an oligosaccharide;
    (B) at least one member selected from the group consisting of adenosine monophosphate and salts thereof,
    wherein the proportion of Component (A) is 0.001 to 0.3 parts by weight per part by weight of Component (B), and the proportion of Component (B) is 0.1 to 10 wt %.

13. A whitening process, moisturizing process or skin anti-aging process comprising applying to skin the composition for external use of claim 9, 10 or 12.

* * * * *